United States Patent
Le Floch et al.

(10) Patent No.: US 11,134,550 B2
(45) Date of Patent: *Sep. 28, 2021

(54) LIGHTING DEVICE THAT FACILITATES READING

(71) Applicants: Université de Rennes 1, Rennes (FR); Albert Le Floch, Rennes (FR)

(72) Inventors: Albert Le Floch, Rennes (FR); Guy Ropars, Rennes (FR)

(73) Assignees: Université de Rennes 1, Rennes (FR); Albert Le Floch, Rennes (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/765,085

(22) PCT Filed: Aug. 3, 2018

(86) PCT No.: PCT/FR2018/052012
§ 371 (c)(1),
(2) Date: May 18, 2020

(87) PCT Pub. No.: WO2019/097128
PCT Pub. Date: May 23, 2019

(65) Prior Publication Data
US 2020/0359479 A1    Nov. 12, 2020

(30) Foreign Application Priority Data
Nov. 20, 2017    (FR) ...................................... 1701200

(51) Int. Cl.
*H05B 45/37*    (2020.01)
*H05B 47/16*    (2020.01)
(Continued)

(52) U.S. Cl.
CPC ............. *H05B 45/37* (2020.01); *A61B 5/165* (2013.01); *G02B 27/021* (2013.01);
(Continued)

(58) Field of Classification Search
None
See application file for complete search history.

(56) References Cited

U.S. PATENT DOCUMENTS

| | | | | |
|---|---|---|---|---|
| 8,076,858 | B2 * | 12/2011 | Cheng .................... | H05B 45/22 315/153 |
| 2006/0279709 | A1 * | 12/2006 | Yamamoto ......... | G03B 21/2013 353/85 |

(Continued)

FOREIGN PATENT DOCUMENTS

WO    2019097128 A1    5/2019

OTHER PUBLICATIONS

Foreign Communication from a Related Counterpart—International Search Report and Written Opinion, dated Oct. 22, 2018, PCT/FR2018/052012, filed Aug. 3, 2018.

(Continued)

*Primary Examiner* — Jany Richardson

(57) ABSTRACT

The invention relates to a device (LIGHT) for lighting a graphic and/or textual content present on any medium and in particular on a paper medium. The lighting device (LIGHT) is configured to periodically activate and deactivate said lighting beam in successive cycles carried out at a preset frequency Fd. Each cycle has a duration T and comprises a period of activation of the light beam of duration T1 followed by a period of deactivation of the light beam of duration T2 or vice versa. The frequency Fd is comprised in an interval of values ranging from 60 to 90 Hz and the duration T1 of the periods of activation of the light beam is comprised in an interval of values ranging from 15 to 30% of the duration T of the cycles.

13 Claims, 1 Drawing Sheet

(51) Int. Cl.
  *H05B 45/305* (2020.01)
  *G02B 27/02* (2006.01)
  *A61B 5/16* (2006.01)
  *F21Y 115/10* (2016.01)

(52) U.S. Cl.
  CPC .......... *H05B 45/305* (2020.01); *H05B 47/16* (2020.01); *F21Y 2115/10* (2016.08)

(56) References Cited

U.S. PATENT DOCUMENTS

| | | | | |
|---|---|---|---|---|
| 2011/0006707 A1* | 1/2011 | Baaijens | ................. | H05B 45/22 315/307 |
| 2013/0021386 A1 | 1/2013 | Min et al. | | |
| 2013/0141017 A1 | 6/2013 | Esaki et al. | | |
| 2014/0228914 A1* | 8/2014 | van de Ven | .......... | A61N 5/0618 607/88 |
| 2015/0078743 A1* | 3/2015 | Yang | ................. | H04B 10/07955 398/38 |
| 2015/0282277 A1* | 10/2015 | Lewis | .................... | H05B 45/20 340/815.45 |
| 2016/0302271 A1* | 10/2016 | Fruitman | ............. | H05B 47/105 |

OTHER PUBLICATIONS

Foreign Communication from a Related Counterpart—French Search Report, dated Aug. 1, 2018, FR Application No. 1701200, filed Nov. 20, 2017.

Albert, Le Floch et al: "Left-right asymmetry of the Maxwell spot centroids in adults without and with dyslexia", Biological Sciences, vol. 284, No. 1865, Oct. 25, 2017 (Oct. 25, 2017), p. 20171380, XP055490044, ISSN 0962-8452, DOI: 10.1098/rspb.2017.1380 p. 7-p. 8; figure 6.

La vraie démocratie: "Des physiciens de Rennes ont percé le mystère de la dyslexie", Youtube, Oct. 19, 2017 (Oct. 19, 2017), p. 2 pp., XP054978716, Extrait de l'Internet: URL:https//www.youtube.com/watch?v=12EoF5YS8Zg [extrait le Sep. 27, 2018] from 2:23 to 3:15.

Albert Le Floch et al: "Left-right asymmetry of the Maxwell spot centroids in adults without and with dyslexia Eleczronic Supplement Material", Oct. 18, 2017 (Oct. 18, 2017) pp. 2-3, XP055510300 Extrait de l'Internet: URL: http://rspb.royalsocietypublishing.org/highwire/filestream/77828/field_highwire_adjunct_files/0/rspb20171380supp1.pdf [extrait le Sep. 26, 2018] p. 2-p. 3; figures S1a-c, S2a-c.

* cited by examiner

LIGHTING DEVICE THAT FACILITATES READING

CROSS-REFERENCE TO RELATED APPLICATIONS

The present application is a filing under 35 U.S.C. 371 as the National Stage of International Application No. PCT/FR2018/052012, filed Aug. 3, 2018, entitled "LIGHTING DEVICE THAT FACILITATES READING," which claims priority to French Application No. 1701200 filed with the Intellectual Property Office of France on Nov. 20, 2017, both of which are incorporated herein by reference in their entirety for all purposes.

FIELD OF THE INVENTION

The present invention relates to a lighting device. The invention relates more particularly to a lighting device facilitating the reading of content, in particular textual, for people suffering from dyslexia.

PRIOR ART

Dyslexia is commonly defined as a set of reading disorders that appear during childhood. They are specific learning disorders, the causes of which appear to be complex and have been and continue to be the subject of numerous studies in various fields.

It is generally out of the question to consider that the causes of dyslexia can be only of a sensory, social or psychological nature.

Studies carried out in the field of neurosciences allow to think that it may be a specific neurological disorder.

The progress made in the field of medical imaging has been able to bring to light the role of certain zones of the brain in the processes of reading and of mastery of language.

The solutions provided to treat the disorders of dyslexia are based on work and play activities according to the difficulties specific to each subject. The goal of such support is to provide the subject suffering from disorders with an independence in terms of reading. The known methods are developed around works in fields such as psychology, psychomotor education and orthoptics, for example.

Recently, studies were carried out, establishing a correlation between particularities specific to the mechanism of vision and the presence of specific disorders of dyslexia. The publication "Left-right asymmetry of the Maxwell spot centroids in adults without and with dyslexia (Le Floch A, Ropars G. 2017, Proc. R. Soc. B 284: 20171380, http://dx.doi.org/10.1098/rspb.2017.1380) mentions the role of the foveas, located in the human eye, in the construction of the images perceived, in the brain, and the fact that characteristics identical or substantially identical for the two eyes of the same subject cause in said subject dysfunctions in the process of vision and phonological processing in the brain. The transmission of a mirror image from one hemisphere to the other, for example, substantially disturbs the process of reading graphic elements or textual content in subjects having disorders characteristics of dyslexia. Disorders related to an instability of focusing and/or a posturological instability, or defects in binocular convergence related to the oculomotor muscles, can also cause visual crowding like the mirror effect.

SUMMARY OF THE INVENTION

The invention allows to improve at least some of the disadvantages of the prior art by proposing a lighting device adapted to facilitate the reading of content, such as graphic content, on any type of support, and in particular on a paper support. The proposed device carries out successive periods of activation and of deactivation or elimination of a light beam in the spectrum of visible light. The light beam is thus activated and deactivated (eliminated) periodically from the lighting device according to successive cycles carried out at a predetermined frequency and comprised in an interval of values ranging from 60 to 90 Hz, via a tunable system thus functioning as an anti-crowding device. This system takes advantage of the Hebbian mechanisms in the neurons of the cortex. The successive periods of activation each have a duration comprised in an interval of values ranging from 15 to 30% of the total duration of the cycles carried out.

The invention relates more particularly to a lighting device comprising a control unit and a lighting module adapted to the generation of a light beam in a spectrum of visible light, characterised in that said lighting device is configured to periodically activate and deactivate said lighting beam according to successive cycles carried out at a predetermined frequency Fd, each cycle having a duration T and comprising a period of activation of the light beam having a duration T1 preceded or followed by a period of deactivation of the light beam having a duration T2, in that the frequency Fd is comprised in an interval of values ranging from 60 to 90 Hz, and in that the duration T1 of the periods of activation of the light beam is comprised in an interval of values ranging from 15 to 30% of the duration T of the cycles.

According to the invention, "deactivation" of the light beam means a total absence of emission of the light beam or an emission having a power much lower than the level of emission of the activation phase, so that the difference in perception that results therefrom causes effects, on a dyslexic subject, similar to the effects discovered because of the absence of beams according to the cycles described above. The deactivation of the light beam can thus be total (the light beam is totally absent after deactivation) or partial.

According to one embodiment of the invention, the predetermined frequency Fd of the light beam is defined by a user of the lighting device.

According to one embodiment of the invention, the predetermined frequency of the light beam is selected discretely, that is to say from a plurality of predetermined frequencies in the aforementioned interval of frequencies.

According to one embodiment of the invention, the frequency Fd varies over time, in order to facilitate even more, in certain cases, the deletion of the visual crowding and the binocular stability.

According to one embodiment of the invention, the frequency Fd varies by increasing by successive steps up to a maximum value according to a first speed, called increasing speed, then varies by decreasing by successive steps down to a minimum value according to a second speed, called decreasing speed, the increasing and decreasing variations repeating iteratively over time.

According to one embodiment of the invention, said decreasing speed is equal to said increasing speed.

According to one embodiment of the invention, said successive steps have equal durations.

According to one embodiment of the invention, said successive steps vary in duration so that the value of said frequency Fd changes according to a waveform in the shape of a triangle, a saw, or a sinusoid between said maximum value and said minimum value.

According to one embodiment of the invention, the duration T1 of the periods of activation of the light beam vary over time.

According to one embodiment of the invention, the beam created in a spectrum of visible light is generated using one or more elements of the LED type. Advantageously, the use of a range of frequencies starting at 60 Hz allows to eliminate the effects of flashing perceptible by the eye of a human being, the limit of perception of the flashing by the eye being located at around 60 Hz, for a human being (without considering animal species and insects).

Advantageously, the alternation of periods of activation and of deactivation (or elimination, or substantial attenuation, or inhibition) of the light beam, established in the spectrum of visible light and applied to (oriented towards) a support, allows a "focusing" of the brain of a subject looking at this illuminated support on an image representative of the content shown on the support observed, then a disappearance of almost disappearance of this same image from the view of the subject before it is transmitted in the form of a mirror image between one hemisphere of the brain and the other hemisphere of the brain of this subject looking at this illuminated support. The time required for the brain to transmit an image, perceived by the eye, between one hemisphere and the other hemisphere, in the form of a mirror image for the latter, is approximately 10 ms.

Thus, the brain prefers the transmitted image over its mirror image, and the confusion existing in the subject who has a strong similarity in the characteristics of their two foveas is lesser or substantially reduced for the reading of the content (graphic and/or textual) shown on the support, in particular when this content is representative of one or more textual contents.

Advantageously, the use of a switch configured to selectively obtain a permanent light beam (ordinary lighting) and a non-permanent light beam (lighting according to the invention) allows a user suffering from dyslexic disorders to compare their usual reading performance (obtained with ordinary lighting) to their performance obtained under electronic control of the light beam according to the invention, after optional optimisation of their own parameters (parameters of frequency and of duty cycle allowing the user to obtain better reading comfort).

LIST OF THE DRAWINGS

The invention will be better understood and other particularities and advantages will appear upon reading the following description, the description referring to the appended drawings in which.

DETAILED DESCRIPTION OF EMBODIMENTS OF THE INVENTION

Figure 2:
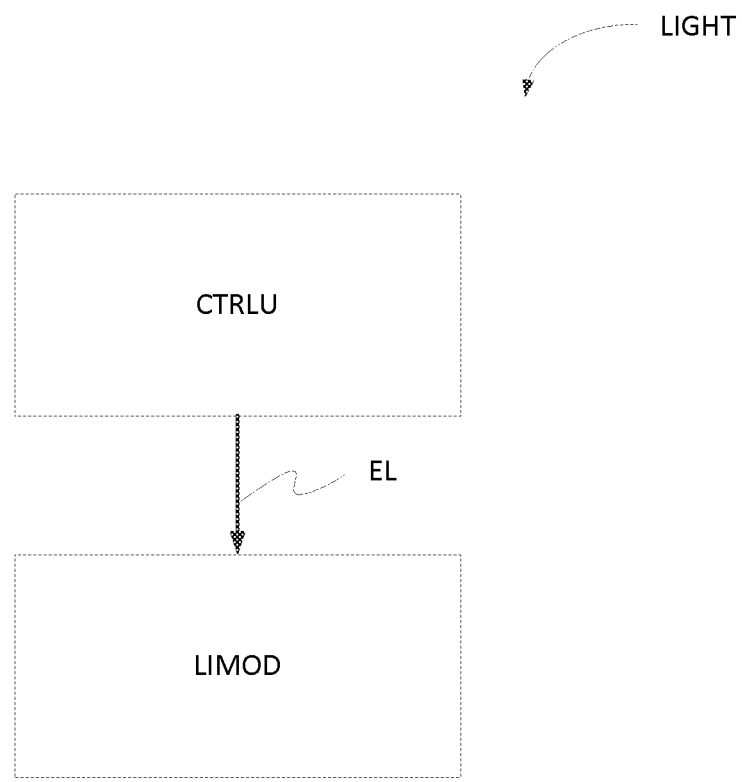
FIG. 2 is a structural diagram of the architecture of a lighting device LIGHT according to a specific and non-limiting embodiment of the invention.

In FIG. 2, the modules shown are functional units, which do or do not correspond to physically distinguishable units. For example, these modules or some of them are grouped together into a single component. On the other hand, according to other embodiments, certain modules are composed of physically separate entities.

Figure 1:
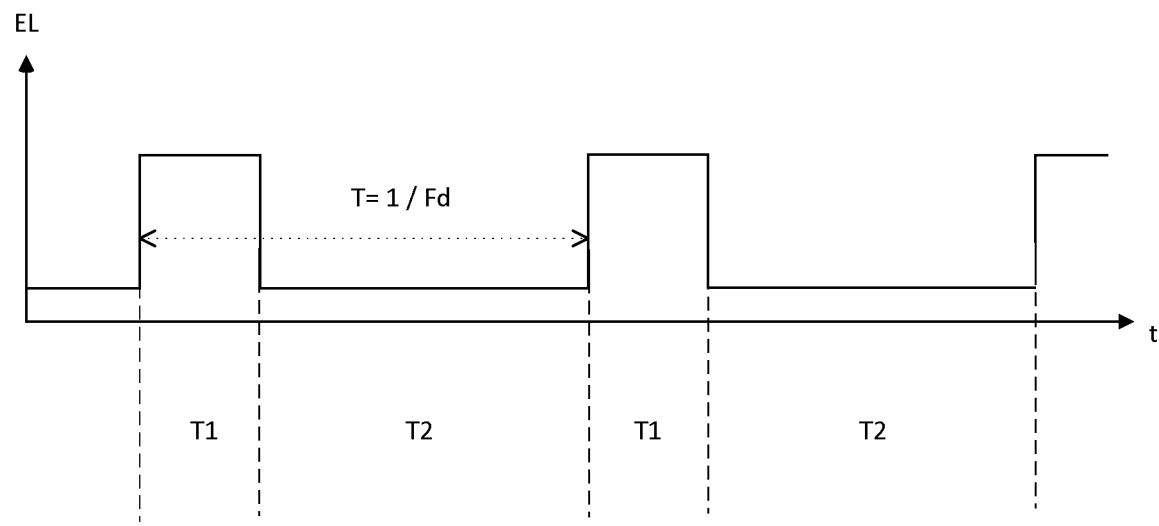
FIG. 1 is a diagram showing a signal EL for controlling a lighting module according to a specific and non-limiting embodiment of the invention.

FIG. 1 is an image, over time, of a signal EL for controlling activation and deactivation (elimination) of a light beam in the spectrum of visible light, in a lighting device LIGHT, according to a specific and non-limiting embodiment of the invention. The signal EL varies over time t and periodically takes on two successive states. According to the preferred embodiment, an assertion of the signal EL in the high state controls an activation of the lighting beam of the lighting device LIGHT capable of thus lighting in a discontinuous manner a graphic and/or textual content on any support, such as a book, for example. The signal EL deactivates (eliminates or inhibits) the light beam of the lighting module when it is positioned in the low state. The signal EL is a periodic signal having a predetermined frequency Fd such that $Fd=1/(T1+T2)$. T1 is the period of activation of the light beam in the spectrum of visible light, or the period of lighting of a support carrying a pattern representing a graphic and/or textual content towards which the beam is oriented. T2 is the period, called deactivation period, during which the beam is eliminated or made inactive, or in other words the period during which the graphic and/or textual content on a support towards which the beam is oriented is no longer illuminated by the beam. The terms "graphic content" should be interpreted here as any content shown on any support, in particular in paper format but not only, and consisting of elementary elements such as for example juxtaposed points or pixels, so that the content shows elements having various shapes and in particular one or more textual contents constructed from signs or symbols of one or more alphabets.

Thus the textual content affixed onto a support corresponds here to a content that can be interpreted in one or more languages, capable of being read and interpreted by a subject, user of the lighting device, positioned in such a way as to look at the support thus illuminated for an operation of reading or of viewing. Such a device is, for example, a table lamp, a torch, a headlamp, a pen light, a pocket lamp, a telephone lamp, a smartphone lamp, a torch watch, a keyring lamp, a ceiling light, a standard lamp, a lightbulb, a lighting tube, a projector, a motor vehicle projector, an overhead projector, a luminous wall coating, a light-up rug, a light-up bracelet, a light-up frame, a mini-lamp to be positioned on a book via an attachment system, a device configured for interior lighting (of a premises) or a device configured for exterior lighting, urban or not. This list of example is not exhaustive. According to the preferred embodiment of the invention, the duty cycle $T1/(T1+T2)$ between the periods of activation and of deactivation (or inhibition) of the light beam, respectively having durations T1 and T2, has a value of between 15% and 30% of the cycle, and the frequency Fd of variation of the signal EL is between 60 Hz and 90 Hz.

Preferably, the frequency of the signal is equal to 70 Hz or 84 Hz and the duty cycle $T1/(T1+T2)$ is equal to 20%.

Advantageously, the control signal EL can be easily forced in a prolonged manner into its state associated with an activation of the light beam, which corresponds to a disengagement of the lighting method implemented in the device LIGHT according to the invention. It would thus be possible to not implement the method for controlling a light beam, in a lighting device according to the invention, in the case in which, for a non-dyslexic subject, a visual discomfort appears because of the discontinuity of activation of the lighting beam.

Advantageously, it is possible to refine the adjustment of the frequency Fd in the interval of values described with the goal of adapting the period T to the sensitivity of a user of the lighting device LIGHT, in the range of frequencies indicated. Indeed, each individual has a specific sensitivity in terms of vision and perceives variations in frequency in a light beam more or less. Thus, a fine adjustment can be made accessible to the user via an adjustment button, a cursor, implemented physically or via any given user interface (graphic elements of a menu on a control screen, for example).

FIG. 2 is a structural representation of a lighting device LIGHT according to a specific and non-limiting embodiment of the invention. This drawing shows the overall architecture of the lighting device LIGHT, also commonly called "lamp". The device LIGHT comprises two main modules which are a control unit CTRLU and a lighting module LIMOD. The control unit CTRLU is the core of the system in terms of control and comprises a conventional bistable circuit (or chopper), adapted to the generation of the signal EL. The bistable chopping circuit of the control unit CTRLU delivers the signal EL characterised by the frequency Fd and by its duty cycle $T1/(T1+T2)$. Of course the control unit CTRLU comprises all the usual elements implemented in such an architecture, such as, for example, one or more operational amplifiers, resistors and capacitors, one or more diodes, a power supply, a zeroing circuit, a circuit for monitoring power supply, a power interface, a current amplifier; the list of these elements is not exhaustive. The architectural details of the control unit CTRLU are not further described insofar as the latter are not useful to the comprehension of the invention. According to one embodiment of the invention, the module CTRLU comprises a bistable circuit built around an operational amplifier, coupled with a current-amplification circuit. Advantageously, the use of a current amplifier allows to obtain an average energy sufficient for proper lighting even though the light beam thus generated is discontinuous. The lighting module LIMOD is a lighting module adapted to the generation of a light beam in the spectrum of visible light, or substantially broader. Advantageously, the beam can be more or less focused to be thus configured for the lighting of a more or less large surface. Such focusing can be carried out by the use of optical elements (lenses) or of mechanical elements (diaphragms), or both at the same time.

Advantageously, the light beam is created from one or more electroluminescent objects of the LED type, from the acronym "Light-Emitting Diode". Of course, the light beam can be made from other light elements, as long as the deactivation of the beam can be sufficiently fast to respect the cycles comprising periods of lighting and of inhibition of the beam (periods of non-lighting).

The term "inhibition of the beam" must be interpreted here as a total disappearance of the beam or a significant lessening of the level of lighting produced by the beam.

It is the capacity to successively activate and inhibit the lighting of a support that presents one or more graphic and/or textual contents, under the control of the bistable module of the unit CTRLU, that advantageously allows the brain of a subject to favour an image rather than its mirror image, perceived using the support when the latter is illuminated by the lighting device LIGHT according to the invention. Advantageously, this allows to significantly aid in the reading and the decryption of textual content, in a subject having dyslexic disorders.

Advantageously, the control unit CTRLU comprises at the output a signal EL for activation (or for turning off/inhibition) of the lighting beam, connected at the input of the lighting module LIMOD.

In other words, the variations in the signal for controlling the lighting beam EL, carried out by the control unit CTRLU comprising a bistable circuit, at a frequency Fd, allow to act on the lighting of a graphic content shown on any given support, so that this graphic content is successively illuminated then less (or not at all) illuminated, periodically, on the support, according to successive cycles having a total length T carried out at a predetermined frequency Fd. According to the invention, the successive periods of lighting T1 each have a duration comprised in an interval of values ranging from 15 to 30% of the duration T of said cycles. The frequency Fd of the cycles (each comprising a period of activation of the beam and a period of deactivation of the beam) is between 60 and 90 Hz.

According to one embodiment, the frequency Fd is fixed.

According to another embodiment, the frequency Fd varies over time.

According to a specific embodiment, the frequency Fd varies by increasing by successive steps up to a maximum value according to a first speed, called increasing speed, then varies by decreasing by successive steps down to a minimum value according to a second speed, called decreasing speed, the increasing and decreasing variations repeating iteratively over time.

According to a specific embodiment, the decreasing speed is equal to the increasing speed.

According to a specific embodiment, the successive steps have equal durations.

According to another specific embodiment, the successive steps vary in duration so that the value of said frequency Fd changes according to a waveform in the shape of a triangle, a saw, or a sinusoid between said maximum value and said minimum value.

Advantageously the duration T1 of the periods of activation varies over time by changing continuously or discontinuously between limit values ranging from 15 to 30% of the duration T of the cycles. Here, "continuously" means a change by increments of the successive steps having equal durations.

The phenomenon of wobulation thus created and applied to the predetermined frequency Fd (variation in the frequency Fd) allows to scan a large number of frequencies between 60 Hz and 90 Hz, some of which are more effective for aiding the reading. These more effective frequencies vary according to the dyslexic subject. By scanning all the frequencies between 60 and 90 Hz, the device of the invention does not require any previous adjustment and becomes effective for a large number of users. This phenomenon of wobulation thus allows, in certain cases, to reduce even more the troubles related to dyslexic disorders.

The same advantage results from the variations in the duration T1 of the periods of activation of the light beam.

According to anther embodiment of the invention, the lighting device LIGHT is configured to generate a first continuous light beam over its entire duration of use and a mobile or filtering device, controlled or moved, periodically masks or inhibits the light beam so that a second beam is generated with characteristics of frequency and of duty cycle such as those described above (Fd between 60 Hz and 90 Hz and $T1/(T1+T2)$ between 15 and 30%. As non-limiting examples, according to this embodiment, a first beam can be interrupted cyclically by a rotary element having solid surfaces and hollow surfaces, or opaque surfaces and translucent surfaces, adapted, by their rotation, to generating the second beam, the effect of which is thus the same as that described in the first embodiment described above.

The invention is not limited to only the embodiments described above, but applies to any device for lighting a graphic and/or textual content on any given support, implementing successive operations of activation of a lighting beam and of inhibition of this same beam, periodically, according to successive cycles carried out at a predetermined frequency Fd between 60 Hz and 90 Hz such that the successive periods of lighting T1 each have a duration comprised in an interval of values ranging from 15 to 30% of the duration T of the cycles carried out.

The invention claimed is:

1. Lighting device (LIGHT) for facilitating the reading of graphic and/or textual content on any given support by dyslexic subjects, said device comprising a control unit (CTRLU) and a lighting module (LIMOD) adapted to the generation of a light beam in a spectrum of visible light, said lighting device (LIGHT) being configured to periodically activate and deactivate said lighting beam according to successive cycles carried out at a predetermined frequency (Fd) that is a reciprocal of the sum of a period of activation of the light beam and of a period of deactivation of the light beam, each cycle having a duration T and comprising a period of activation of the light beam having a duration T1 preceded or followed by a period of deactivation of the light beam having a duration (T2), Fd being such that Fd=1/(T1+T2), said device being characterised in that the frequency (Fd) is comprised in an interval of values ranging from 60 to 90 Hz, and in that the duration (T1) of the periods of activation of the light beam is comprised in an interval of values ranging from 15 to 30% of the duration (T) of the cycles.

2. Lighting device according to claim 1, wherein said frequency (Fd) varies over time.

3. Lighting device according to claim 2, wherein said predetermined frequency (Fd) is called wobulation frequency, takes advantage of the Hebbian mechanisms of the neurons of the cortex and varies by increasing by successive steps up to a maximum value according to a first speed, called increasing speed, then varies by decreasing by successive steps down to a minimum value according to a second speed, called decreasing speed, the increasing and decreasing variations repeating iteratively over time.

4. Lighting device according to claim 3, wherein said decreasing speed is equal to said increasing speed.

5. Lighting device according to claim 4, wherein said successive steps have equal durations.

6. Lighting device according to claim 4, wherein said successive steps vary in duration so that the value of said frequency (Fd) changes according to a waveform in the shape of a triangle, a saw, or a sinusoid between said maximum value and said minimum value.

7. Lighting device according to claim 1, wherein the duration T1 of said periods of activation of the light beam vary over time.

8. Lighting device according to claim 1, wherein said light beam is generated using one or more elements of the LED type.

9. Lighting device according to claim 1, characterised in that it is of a type comprised in the list: a table lamp, a torch, a headlamp, a pen light, a pocket lamp, a telephone lamp, a smartphone lamp, a torch watch, a keyring lamp, a ceiling light, a standard lamp, a lightbulb, a lighting tube, a projector, a motor vehicle projector, an overhead projector, a luminous wall coating, a light-up rug, a light-up bracelet, a light-up frame, a mini-lamp to be positioned on a book, a device configured for interior lighting or a device configured for exterior lighting, urban or not.

10. Lighting device according to claim 1, wherein said frequency (Fd) is equal to 70 Hz or 84 Hz and the duty cycle T1/(T1+T2) is equal to 20%.

11. Lighting device according to claim 1, characterised in that it is a table lamp or a mini-lamp to be positioned on a book.

12. Method for facilitating the reading of graphic and/or textual content on any given support by a dyslexic subject, characterised in that it implements a lighting device as defined according to claim 1 that is periodically activated and deactivated according to successive cycles carried out at a predetermined frequency Fd, each cycle having a duration T and comprising a period of activation of the light beam having a duration T1 preceded or followed by a period of deactivation of the light beam having a duration T2, the frequency Fd being defined by the equation Fd=1/(T1+T2), Fd being comprised in an interval of values ranging from 60 to 90 Hz, and the duration T1 of the periods of activation of the light beam being comprised in an interval of values ranging from 15 to 30% of the duration T of the cycles.

13. Method for facilitating the reading of graphic and/or textual content according to claim 12, wherein said predetermined frequency (Fd) is defined by a user of said lighting device.

* * * * *